(12) United States Patent
Bagger-Sjöbäck et al.

(10) Patent No.: US 11,602,466 B2
(45) Date of Patent: Mar. 14, 2023

(54) ABSORBENT HYGIENIC ARTICLE FOR ABSORBING BODY FLUIDS

(71) Applicant: Essity Hygiene and Health Aktiebolag, Gothenburg (SE)

(72) Inventors: Anna Bagger-Sjöbäck, Gothenburg (SE); Magdalena Hörle, Gothenburg (SE); Philip Blomström, Gothenburg (SE); Lars Fingal, Gothenburg (SE); Anna Nihlstrand, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/783,335

(22) PCT Filed: Dec. 20, 2019

(86) PCT No.: PCT/SE2019/051331
§ 371 (c)(1),
(2) Date: Jun. 8, 2022

(87) PCT Pub. No.: WO2021/126035
PCT Pub. Date: Jun. 24, 2021

(65) Prior Publication Data
US 2023/0042528 A1 Feb. 9, 2023

(51) Int. Cl.
*A61F 13/15* (2006.01)
*A61F 13/511* (2006.01)
(Continued)

(52) U.S. Cl.
CPC .. *A61F 13/51121* (2013.01); *A61F 13/51104* (2013.01); *A61F 13/51401* (2013.01);
(Continued)

(58) Field of Classification Search
CPC .......... A61F 13/15203; A61F 13/51104; A61F 13/51108; A61F 13/51401;
(Continued)

(56) References Cited

U.S. PATENT DOCUMENTS

| 5,486,167 A | 1/1996 | Dragoo et al. |
| 6,017,833 A | 1/2000 | Reiner et al. |

(Continued)

FOREIGN PATENT DOCUMENTS

| CN | 1126067 A | 7/1996 |
| CN | 1137585 A | 12/1996 |

(Continued)

OTHER PUBLICATIONS

International Preliminary Report on Patentability (PCT/IPEA/409) dated Mar. 2, 2022 for International Application No. PCT/SE2019/051330. (7 pages).

(Continued)

*Primary Examiner* — Catharine L Anderson
(74) *Attorney, Agent, or Firm* — Buchanan Ingersoll & Rooney PC

(57) ABSTRACT

An absorbent hygienic article for absorbing body fluids, the article including a liquid permeable topsheet, a backing layer and an absorbent core arranged between the topsheet and the backing layer, the topsheet and the backing layer being made from roll materials. The topsheet or an absorbent layer in the absorbent core is constituted by a cellulosic fibrous web, the fibres in the cellulosic fibrous web being constituted by a mixture of cellulose fibres including regenerated cellulose fibres or natural cellulose staple fibres and cellulose pulp fibres, the cellulosic fibrous web being a foam-formed, hydroentangled fibrous web.

18 Claims, 1 Drawing Sheet

(51) Int. Cl.
*A61F 13/514* (2006.01)
*D04H 1/4258* (2012.01)
*D04H 1/4382* (2012.01)
*D04H 1/492* (2012.01)
*D04H 1/68* (2012.01)
*A61F 13/53* (2006.01)
*A61F 13/47* (2006.01)
*A61F 13/51* (2006.01)

(52) U.S. Cl.
CPC ....... *D04H 1/4258* (2013.01); *D04H 1/43835* (2020.05); *D04H 1/492* (2013.01); *D04H 1/68* (2013.01); *A61F 2013/15406* (2013.01); *A61F 2013/15447* (2013.01); *A61F 2013/15983* (2013.01); *A61F 2013/4708* (2013.01); *A61F 2013/51021* (2013.01); *A61F 2013/51134* (2013.01); *A61F 2013/530481* (2013.01); *D10B 2509/026* (2013.01)

(58) Field of Classification Search
CPC .. A61F 2013/15406; A61F 2013/15414; A61F 2013/15447; A61F 2013/51019; A61F 2013/51021; A61F 2013/51134; A61F 2013/530036; A61F 2013/530481
See application file for complete search history.

(56) References Cited

U.S. PATENT DOCUMENTS

| | | | |
|---|---|---|---|
| 9,161,865 B2 * | 10/2015 | Paveletzke | ........ A61F 13/49017 |
| 2003/0213108 A1 | 11/2003 | Strandqvist | |
| 2005/0155199 A1 | 7/2005 | Stralin et al. | |
| 2014/0170402 A1 | 6/2014 | Knowlson et al. | |
| 2015/0083354 A1 | 3/2015 | Strandqvist | |
| 2017/0203542 A1 | 7/2017 | Ramaratnam et al. | |
| 2018/0355527 A1 | 12/2018 | Strandqvist et al. | |
| 2018/0363177 A1 | 12/2018 | Strandqvist | |
| 2019/0276958 A1 | 9/2019 | Konishi | |

FOREIGN PATENT DOCUMENTS

| | | |
|---|---|---|
| CN | 100558980 C | 11/2009 |
| CN | 103118646 A | 5/2013 |
| CN | 11191692 A | 8/2019 |
| EP | 3382078 A1 | 10/2018 |
| JP | H1193055 A | 4/1999 |
| WO | 9602701 A1 | 2/1996 |
| WO | 03069038 A1 | 8/2003 |
| WO | 03083197 A1 | 10/2003 |
| WO | 2005002842 A1 | 1/2005 |
| WO | 2005042819 A2 | 5/2005 |
| WO | 2006001739 A1 | 1/2006 |
| WO | 2010021572 A1 | 2/2010 |
| WO | 2012090130 A2 | 7/2012 |
| WO | 2012150902 A1 | 11/2012 |
| WO | 2017079169 A1 | 5/2017 |
| WO | 2018065668 A1 | 4/2018 |

OTHER PUBLICATIONS

International Preliminary Report on Patentability (PCT/IPEA/409) dated Mar. 2, 2022 for International Application No. PCT/SE2019/051331. (8 pages).
International Search Report (PCT/ISA/210) and Written Opinion (PCT/ISA/237) dated Sep. 2, 2020, by the Swedish Patent Office as the International Searching Authority for International Application No. PCT/SE2019/051330. (16 pages).
International Search Report (PCT/ISA/210) and Written Opinion (PCT/ISA/237) dated Sep. 2, 2020, by the Swedish Patent Office as the International Searching Authority for International Application No. PCT/SE2019/051331. (15 pages).
Written Opinion of the International Preliminary Examining Authority (PCT/IPEA/408) dated Dec. 1, 2021 by the European Patent Office as the International Searching Authority for International Application No. PCT/SE2019/051330. (5 pages).
Written Opinion of the International Preliminary Examining Authority (PCT/IPEA/408) dated Dec. 1, 2021 by the Swedish Patent Office as the International Searching Authority for International Application No. PCT/SE2019/051331. (7 pages).
Corrected International Search Report (PCT/ISA/210), Corrected Written Opinion (PCT/ISA/237), Communication in Cases for Which No Other Form is Applicable (PCT/ISA/224) dated Feb. 1, 2021 by the Swedish Patent Office as the International Searching Authority for International Application No. PCT/SE2020/051158. (12 pages).
Office Action issued in Chinese Patent Application No. 201980102567.0, dated Nov. 4, 2022, with English Translation (24 pages).

* cited by examiner

1

ABSORBENT HYGIENIC ARTICLE FOR ABSORBING BODY FLUIDS

TECHNICAL FIELD

The invention pertains to an absorbent hygienic article for absorbing body fluids, the article comprising a liquid permeable topsheet, a backing layer and an absorbent core arranged between the topsheet and the backing layer, the topsheet and the backing layer being made from roll materials.

BACKGROUND

In the field of disposable hygienic articles such as disposable sanitary napkins, panty liners, diapers, incontinence protectors, incontinence garments, and the like which are thrown away after a single use, it is a rising concern to minimize the environmental impact of such articles. Hence, it is a desire that disposable hygienic articles may be made using a minimum of oil based polymeric materials.

However, conventionally used plastic materials have functional advantages, e.g. as they are non-absorbent and provide dry surface materials desirable for articles which are placed in close contact with the skin of a wearer.

An object of the present disclosure may therefore be to offer a hygienic absorbent article having a non-oil based body-contacting material without losing functionality.

A further object may be to provide a hygienic absorbent article which is dry against skin and which efficiently utilizes the available absorption capacity of the hygienic absorbent article.

SUMMARY

One or more of the above objects may be achieved with an absorbent hygienic article in accordance with claim 1. Further embodiments are set out in the dependent claims, in the following description and in the drawings.

An absorbent hygienic article for absorbing body fluids as disclosed herein comprises a liquid permeable topsheet, a backing layer and an absorbent core arranged between the topsheet and the backing layer, the topsheet and the backing layer being made from roll materials. The topsheet is constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the cellulosic fibrous web being a foam-formed, hydroentangled fibrous web. Alternatively, an absorbent layer in the absorbent core is constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the absorbent fibrous web being a foam-formed, hydroentangled fibrous web. A further alternative is that both the topsheet and an absorbent layer in the absorbent core are constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the absorbent fibrous web being a foam-formed, hydroentangled fibrous web.

In the absorbent hygienic articles as disclosed herein, it may be preferred that at least an absorbent layer in the absorbent core is constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the absorbent fibrous web being a foam-formed, hydroentangled fibrous web. The absorbent layer is preferably arranged in direct contact with the topsheet.

The absorbent hygienic article may be any useful type of absorbent article for absorbing bodily excretions including diapers, such as open diapers or pant-type diapers, incontinence garments, incontinence shields, sanitary napkins, panty liners, bed protectors, seat protectors, and the like. The absorbent hygienic article as disclosed herein may also be an integrated absorbent unit in an absorbent hygienic pant-type garment.

The topsheet in an absorbent hygienic article as disclosed herein may be constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the cellulosic fibrous web being a foam-formed, hydroentangled fibrous web.

The topsheet being constituted by a cellulosic fibrous web as set out herein may have a basis weight in the range of from 10 to 30 gsm.

A user-facing surface of the absorbent hygienic article may be provided with a pattern, the pattern being an embossed pattern, a dimpling pattern, a printed pattern or a combination of one or more of an embossed pattern, a dimpling pattern, and a printed pattern.

The absorbent hygienic articles as disclosed herein may have embossings arranged in a user-facing surface of the topsheet. The embossings serve to locally compress the cellulosic fibrous web to create a compacted structure with smaller pores within the areas of the embossings. Such embossings may be used to further control liquid distribution in the absorbent hygienic article. In addition to or instead of functional embossings, the topsheet may be provided with decorative embossings, functional and/or decorative print, etc., as known in the art.

Functional embossings may be provided in an absorbent core layer constituted by a cellulosic fibrous web as disclosed herein to enhance fluid distribution and flow control within the absorbent core layer.

In addition to the topsheet being constituted by a cellulosic fibrous web as set out herein, an absorbent layer in the absorbent core may be constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the absorbent fibrous web being a foam-formed, hydroentangled fibrous web having a basis weight in the range of 30 to 150 gsm. The absorbent layer may preferably be arranged in direct contact with the topsheet.

The topsheet and the backing layer may be joined to each other in a peripheral join to enclose the absorbent core or the topsheet and the backing layer may be made of a single sheet of liquid permeable cover material which is wrapped around the core. Furthermore, the topsheet and the backing layer may be indirectly joined by being directly joined to the absorbent core or another component arranged between the topsheet and the backing layer. Indirect joining of the topsheet and the backing layer may e.g. be employed if all of the topsheet, the backing layer and the absorbent core are made from roll materials. The backing layer may be liquid permeable, e.g. when used in an absorbent insert intended for being placed on top of a liquid permeable topsheet in another absorbent article, such as in a diaper or incontinence garment. Generally, the backing layer is resistant to liquid penetration or liquid impermeable. The backing layer may be a breathable backing layer, as known in the art. It may also be preferred that the backing layer is derived from renewable raw materials.

The absorbent cellulosic fibrous webs which are suitable for use in the absorbent hygienic articles as disclosed herein have a large proportion of the fibres oriented at an angle to the plane of the web such that the fibres extend at least partly in the Z-direction of the web. As used herein the Z-direction of the web is perpendicular to the X-direction and the Y-direction which define the planar extension of the web. The Z-direction is also referred to herein as the thickness direction of the web. The Z-directionality of the fibres in the web may be influenced by the web being a hydroentangled web. Hydroentangling involves exposing the formed web to high-pressure water jets which move fibres out of the plane of the web. Hydroentangling may be performed on one side of the foam-formed web or on both sides. The Z-directionality of the fibres in the web may also be enhanced during wetforming of the web by dewatering the web from both sides, e.g. as disclosed in WO 2018/065668 A1. Depending on the forming wires used and the dewatering speed, the webs formed according to the method in WO 2018/065668 A1 may be provided with a high degree of likesidedness, which may be advantageous in some applications.

The cellulosic fibrous webs as used herein are foam-formed webs. Foam-forming is a type of wet-forming which involves dispersing the fibres in a foamed liquid containing water and a surfactant. Foam-forming creates bulky high porosity webs.

The cellulosic fibrous web may have been foam-formed as a single unitary web which has subsequently been hydroentangled. However, the cellulosic fibrous webs may comprise two or more layers of foam-formed webs which have been hydroentangled together to form a coherent cellulosic fibrous web. In the case where two or more layers of foam-formed webs make up the final hydroentangled web, the layers may have the same or different fibre compositions. Furthermore, the layers may have the same or different basis weights and may have the same or different bulk.

The cellulose pulp fibres in the absorbent fibrous webs used in the absorbent hygienic articles as disclosed herein are preferably wood pulp fibres as wood pulp fibres can be economically manufactured from readily available raw material, are well known in the art and have good absorption and liquid distribution properties. The cellulose pulp fibres are considerably shorter than the regenerated cellulose fibres and/or natural cellulose staple fibres which form a fibrous network for capturing and containing the cellulose pulp fibres.

Wood pulp fibres as referred to herein comprises pulp fibres from chemical pulp, e.g. kraft, sulphate or sulphite, mechanical pulp, thermo-mechanical pulp, chemi-mechanical pulp and/or chemo-thermo-mechanical pulp, abbreviated as CTMP. Pulps derived from both deciduous (hardwood) and coniferous (softwood) can be used. Cellulose pulp fibres may also be derived from non-wood plants, e.g. cereal straws, bamboo, jute or sisal. The fibres or a portion of the fibres may be recycled fibres, which may belong to any or all of the above categories. The fibres may have a natural staple length, such as cotton or may be cut to a desired staple length.

Additives such as softeners, e.g. quaternary ammonium compounds, dry-strength agents or wet-strength agents may be added in order to facilitate manufacturing of the cellulosic fibrous web or to adjust the properties thereof. However, for some embodiments of the cellulosic fibrous web, the absorbent fibrous web may be so strong in itself, that there is no need for a dry strength agent or and/or a wet strength agent to improve strength.

As all the fibres used in the absorbent fibrous webs as disclosed herein are of cellulosic origin, the absorbent fibrous webs as disclosed herein are made from renewable raw materials.

Further, the absorbent fibrous webs as disclosed herein have a textile-like character, which is appreciated in many user situations, e.g. for hygiene articles which are intended to be placed in close contact with the skin of a user. Products, such as panty liners, made of the cellulosic absorbent fibrous webs as disclosed herein may possess the requisite strength properties while at the same time being soft and comfortable against the skin of a user. The textile-like character of the cellulosic fibrous webs may be felt both in a dry and in a wet state.

The regenerated cellulose fibres and/or the natural cellulose staple fibres in the cellulosic fibrous webs used in the absorbent hygienic articles as disclosed herein may be staple fibres having a length within the range of from 2 to 20 millimeter, such as in the range of from 5 to 15 millimeter, such as in the range of from 5 to 12 millimeter, such as in the range of from 6 to 10 millimeter. The fibre density of the regenerated cellulose fibres and/or the natural cellulose staple fibres used in the webs as disclosed herein may be in the range of from 0.3 to 3 dtex, such as in the range of from 0.5 to 2.4 dtex, such as in the range of from 0.8 to 2.0 dtex.

Regenerated cellulose fibres may be viscose fibres or lyocell fibres.

The mixture of cellulose fibres may be constituted by 2 to 50% by weight of regenerated cellulose fibres and/or natural cellulose staple fibres based on a total weight of the mixture of cellulose fibres, preferably such as % by weight of a total weight of the mixture of cellulose fibres, more preferably 5 to 25% by weight of a total weight of the mixture of cellulose fibres, most preferably 10 to 20% by weight of the mixture of cellulose fibres.

A topsheet made from the cellulosic fibrous webs as disclosed herein may have a bulk in the range of from 8 to 17 $cm^3/g$.

An absorbent layer, such as an absorbent core layer made from the cellulosic fibrous webs as disclosed herein may have a bulk in the range of from 8 to 10 $cm^3/g$.

The absorbent hygienic articles as disclosed herein may have a rewet of less than 1 gram, such as a rewet of less than 0.8 gram or a rewet of less than 0.7 gram as measured according to the method disclosed herein.

The absorbent hygienic articles as disclosed herein may have a liquid spreading capacity in a machine direction of the cellulosic fibrous web of 75 millimeters or more as measured after three insults of test liquid in accordance with the test method disclosed herein.

The absorbent hygienic articles as disclosed herein may have a liquid spreading capacity in a cross machine direction of the absorbent hygienic article of 30 millimeters or more as measured after a first insult of test liquid and of 45 millimeters or more as measured after two insults of test liquid, the measurements being made in accordance with the test method disclosed herein.

The machine direction of the sample used in the method corresponds to the length direction of the absorbent hygienic article and the cross machine direction of the sample corresponds to the cross direction or width direction of the absorbent hygienic article.

The absorbent core in the absorbent hygienic articles as disclosed herein may comprise superabsorbent material, such as cellulose based or starch based superabsorbent material.

Exemplary of superabsorbent materials suitable for use in the absorbent hygienic articles as disclosed herein are gelatin; alginates; cellulose based polymers such as methyl cellulose, hydroxymethyl cellulose, carboxymethylcellulose, cellulose acetate phthalate, and the like; starch based polymers such as carboxymethyl starch; natural gums, such as gum arabic, locust bean gum, carrageenan gum, and xanthan gum; pectins; polymers formed from acid-group containing monomers, such as poly-(acrylates) (including poly(acrylic acid), poly(methacrylic acid), and the like), poly (ethers), poly-(acrylamides), poly(vinyl alcohol), maleic anhydride copolymers, poly(vinyl sulfonates), hydrolyzed acrylonitrile grafted starch, acrylic acid grafted starch, poly(N-vinyl pyrrolidone), poly(2-hydroxyethylacrylate), poly(2-hydroxyethylmethacrylate), poly(sodium acrylate-co-acrylic acid), poly(vinylsulfonic acid); poly-(ethyleneoxide), block co-polymers of ethylene oxide with polyamides, polyesters, and polyurethanes, and salt forms, mixtures and copolymers of the above.

BRIEF DESCRIPTION OF THE DRAWINGS

The hygienic articles as disclosed herein will be further explained hereinafter by means of non-limiting examples and with reference to the appended drawings wherein.

DETAILED DESCRIPTION

It is to be understood that the drawings are schematic and that individual components or features, such as layers of material are not necessarily drawn to scale. The panty liner shown in the figures is provided as an example only and should not be considered limiting to the invention as disclosed herein. In particular, it is to be understood that shape and dimensions are non-essential features of the invention and may be varied within the scope of the claims. In the following the claimed absorbent hygienic article is described with reference to a panty liner. As set out herein, the claimed invention is applicable to any other type of absorbent hygienic article comprising a topsheet, a liquid barrier layer and an absorbent core arranged between the topsheet and the liquid barrier layer. The absorbent hygienic articles as disclosed herein are intended for being at least partly placed in the crotch portion of a user of the absorbent hygienic article for absorbing blood, vaginal discharges, urine, feces, etc. The absorbent hygienic articles include sanitary napkins, diapers for children and adults, incontinence protectors, etc.

Figure 1:
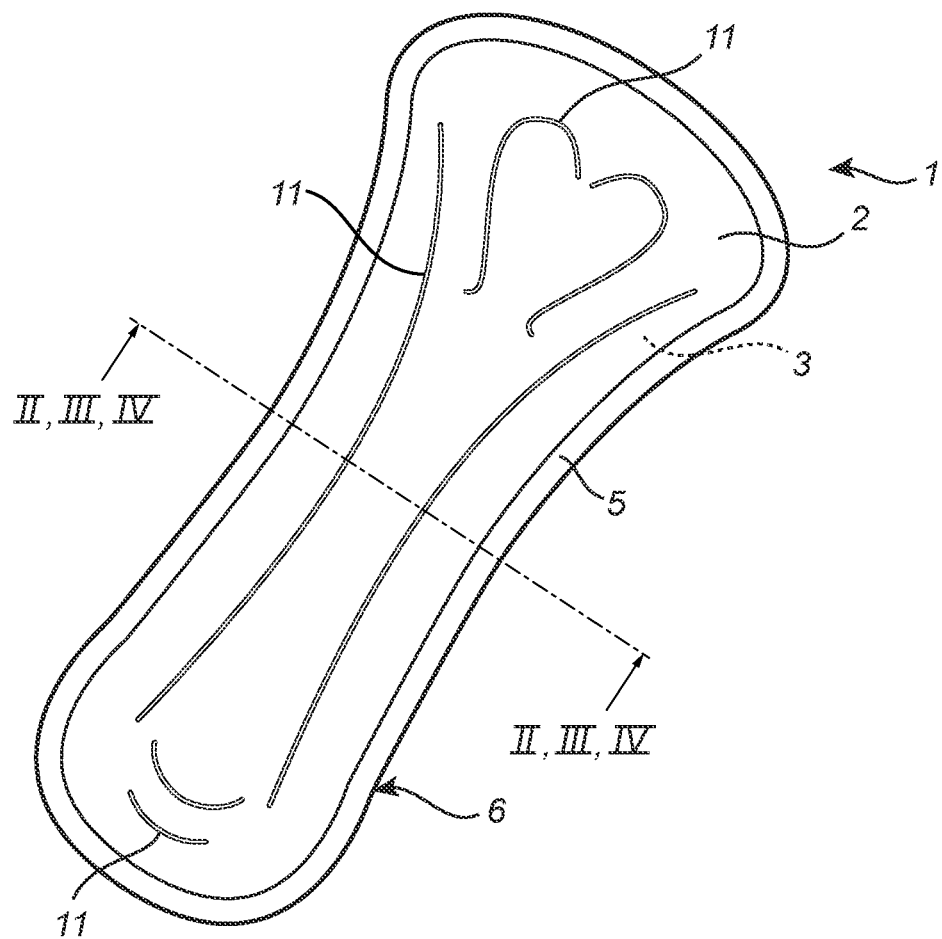
FIG. 1 shows a panty liner.
Figure 2:
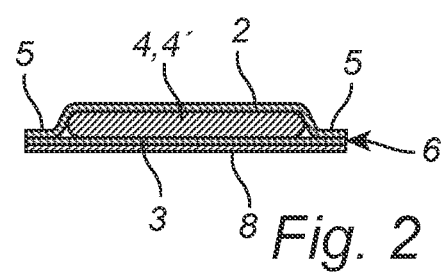
FIG. 2 shows a cross-section taken along the line II-II through the panty liner in FIG. 1.

The absorbent hygienic article 1 which is shown in FIGS. 1 and 2 is a panty liner comprising a liquid-permeable topsheet 2, arranged on the surface of the absorbent hygienic article 1 which is intended to face towards a user during use. The liquid-permeable topsheet 2 is constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the absorbent fibrous web being a foam-formed, hydroentangled fibrous web.

The absorbent hygienic article 1 further comprises a liquid barrier layer 3, arranged on the surface of the absorbent hygienic article 1, which is intended to face away from the user during use, also referred to herein as the garment-facing surface of the absorbent hygienic article 1. The liquid barrier layer 3 is preferably fluid impermeable. However, liquid barrier layer materials that are only resistant to fluid penetration may be used particularly in instances where relatively small amounts of body fluid are expected to be taken up by the absorbent hygienic article as disclosed herein. The liquid barrier layer 3 may be a thin, flexible, liquid impermeable plastic film, but liquid impermeable nonwoven materials, liquid impermeable foams and liquid impermeable laminates are also contemplated for the articles disclosed herein. The liquid barrier layer 3 may be breathable, implying that air and vapor may pass through the liquid barrier layer. Furthermore, the liquid barrier layer 3 may have an outer, garment-facing surface of a textile material such as nonwoven. Further, it may be preferred that the backing layer is made from renewable raw material.

An absorbent core 4 is arranged between the topsheet 2 and the liquid barrier layer 3. In the panty liner 1 which is shown in the FIGS. 2 and 3, the absorbent core 4 is shown as a single cellulosic absorbent layer 4' which is constituted by a mixture of cellulose fibres comprising regenerated cellulose fibres and/or natural cellulose staple fibres and cellulose pulp fibres, the absorbent fibrous web being a foam-formed, hydroentangled fibrous web. The cellulosic absorbent layer 4' is arranged immediately inside the topsheet 2 and in direct contact and fluid communication with the topsheet 2.

In applications where more absorbency is needed such as in larger panty liners, sanitary napkins, diapers, incontinence protectors, incontinence garments, etc. the absorbent hygienic article may comprise further absorbent layers and components, as set out herein.

Figure 4:
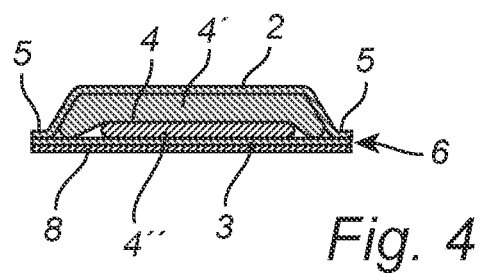
FIG. 4 shows a further alternative cross-section taken along the line IV-IV through the panty liner in FIG. 1.

An example of such an absorbent hygienic article is shown in FIG. 4 where an additional absorbent layer 4" is arranged beneath the cellulosic absorbent layer 4'.

Such additional absorbent layer or layers may comprise superabsorbent material, as set out herein. The superabsorbent material may be in particle form, as superabsorbent foam, superabsorbent fibres, etc. as known in the art. Superabsorbent particles may be blended with cellulose fibres such as cellulose pulp fibres.

In the panty liner 1 which is shown in FIGS. 2 and 4 the topsheet 2 and the liquid barrier layer 3 are directly joined to each other in an edge seal 5 extending around the periphery of the absorbent core 4. The edge seal 5 is formed laterally outside the peripheral edge of the absorbent core 4. Joining of the topsheet 2 and the liquid barrier layer 3 can be achieved using any known technique or combination of techniques suitable for the purpose, such as gluing, thermobonding, ultrasonic welding or heat embossing.

As set out herein, such a direct seal between the topsheet 2 and the liquid barrier layer 3 is an optional feature of the claimed invention. Hence, the topsheet 2 and the liquid barrier layer 3 may be indirectly joined to each other by being directly joined to the absorbent core, or may be formed by a single sheet of material which is wrapped around the absorbent core. In the absorbent hygienic article shown in FIG. 3, all of the topsheet 2, the liquid barrier layer 3 and the absorbent core 4 are coextensive and together define the peripheral edge 6 of the absorbent hygienic article 1, the peripheral edge 6 of the absorbent hygienic article 1 defining the planar shape of the absorbent hygienic article 1.

Figure 3:
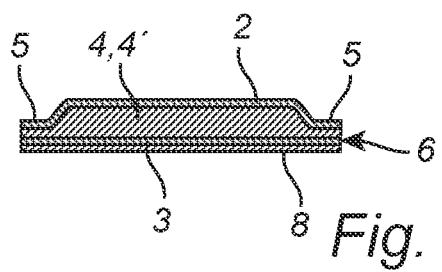
FIG. 3 shows an alternative cross-section taken along the line III-III through the panty liner in FIG. 1.

In the absorbent hygienic article 1 which is shown in FIG. 3, the edge seal 5 joins all of the topsheet 2, the liquid barrier layer 3 and the absorbent core 4. The edge seal 5 in FIG. 3 is a compression bond which may be made by heating and embossing.

The edge seals 5 as disclosed herein may be continuous or discontinuous bonds, as desired.

The components in the absorbent hygienic article 1 may be connected to each other by conventional means such as construction adhesive, heat bonding, ultrasonic bonding, mechanical welding using embossing and pressure, etc. It may not be necessary to bond internal components of the absorbent article to each other by special bonding means. Accordingly, it may suffice that such components are held together by frictional forces.

As is shown in FIGS. 2-4, the absorbent hygienic article 1 has a fastening member 8 on the garment-facing surface 5 of the absorbent hygienic article 1. The fastening member 8 is provided for allowing the absorbent hygienic article 1 to be fastened in the crotch portion of a pair of underpants or a hygienic pant and may e.g. be an adhesive fastening member, a friction fastener member or a hook-type fastener member as known in the art. The fastening member 8 may be protected by a release liner (not shown) during packaging and transport. The release liner is removed to expose the fastening member 8 before the absorbent hygienic article 1 is applied in the crotch portion of a pair of underpants. The fastening member 8 may alternatively be protected by a wrapper, also commonly referred to as a "single pack", which is releasable attached to the fastening member 8 and which is removed at the same time as the absorbent hygienic article 1 is taken out of the wrapper. The fastening member 8 may be applied over the full outer surface of the the liquid barrier layer 3 or may be applied only in one or more selected areas of the outer surface of the liquid barrier layer 3. The fastening member 8 is an optional feature of the absorbent hygienic article.

The absorbent hygienic article 1 which is shown in FIG. 1 is provided with an embossed pattern in the form of a plurality of line embossings 11 which are arranged in the topsheet 2. The embossings 11 are optional features of the absorbent hygienic articles as disclosed herein and are not shown in the cross-sectional views in FIGS. 2-4. The embossings 11 may extend from the outer surface of the absorbent hygienic article 1 downward into the underlying absorbent core 4 such that the fibrous structure of the topsheet 2 and optionally also the absorbent core 4 is compressed within the areas of the embossings. Line embossings generally promote fluid distribution along the lines and counteract fluid distribution perpendicular to the embossings.

The absorbent hygienic article 1 may alternatively or in addition to embossings comprise functional and/or appearance enhancing print. The embossings 11 which are shown in FIG. 1 are optional to the absorbent hygienic article as disclosed herein. It is also to be understood that the embossings are not limited either to the number, shape or positioning shown in FIG. 1. Furthermore, if using embossings, they may be functional, appearance enhancing or a combination of functional and appearance enhancing embossings.

EXAMPLES AND DESCRIPTION OF TEST METHODS

Absorbent articles or isolated layers of the cellulosic fibrous web as disclosed herein can be subjected to testing according to the methods described herein.

Sample Preparation

Before testing, single articles or single layer web samples should rest flat and exposed for 24 hours in a stable laboratory environment set to 23° C. and 50% relative humidity. All subsequent testing should then be made in this same environment.

Determining Basis Weight and Density of a Web Sample

The web sample is weighed to the third decimal. The area of the sample is then determined, and basis weight is obtained by dividing the sample weight by the sample area. Basis weight is reported in the unit $g/m^2$ (gsm).

Web thickness is measured under a pressure of 0.5 kPa. A suitable thickness gauge should have an accuracy of 0.01 mm. Pressure is exerted from a square foot measuring 50×50 mm. The foot is gently lowered onto the sample, and a thickness value is read after 5 seconds.

Bulk is obtained by dividing the sample volume by the sample weight and should be reported in the unit $cm^3/g$.

Density is obtained by dividing the sample weight by the sample volume and should be reported in the unit $kg/m^3$.

A mean value is reported from measurements of ten representative samples.

Determining Spreading Distance and Rewet

An artificial menstrual fluid (AMF) according to the French standard AFNOR Q34-018 is used when testing.

For the spreading and rewet determinations, the sample should rest flat on a laboratory bench. Folded absorbent articles are unfolded, and carefully stretched flat. If testing a fibrous web in isolation, the web should be cut or punched to a rectangle measuring 50×150 mm. The length direction of the sample should coincide with the machine direction (MD) of the web. A smooth, liquid impermeable polyethylene film should be placed underneath the fibrous web.

The center point of the sample is identified (the point where the longitudinal centerline crosses the transverse centerline). AMF is introduced via a tube (internal diameter about 3 mm) connected to an automatic dispenser. The orifice of the tube is positioned perpendicular to the center point, with about 5 mm distance to the sample surface.

The sample is subjected to three 1.0 ml doses of AMF (i.e. 3.0 ml in total), introduced at a rate of 15 ml/min. When a dose has been absorbed (i.e. when there is no more free fluid on the sample surface), a stopwatch is started, and the next dose is introduced after 15 minutes.

Spreading length is measured 5 seconds after each dose has been absorbed. A ruler is placed along the longitudinal and transverse centerlines of the sample, and the extension of the wet area in the fibrous web (or article top layer) is determined. AMF that possibly spreads longer in the lateral side regions along the respective centerlines (such as in grooves or densified bonding patterns) is disregarded.

Rewet is measured 15 minutes after the third (last) dose has been absorbed. A stack of five pre-weighed filter papers (90×120 mm, 440 $g/m^2$ per sheet, Quality 167 from Munktell Ahlstrom or equivalent filter papers) is centered on top of the sample. A 5.5 kg weight with bottom dimension 90×120 mm (exerting a pressure of 5 kPa) is gently lowered on top of the stack. After 15 seconds the weight is removed, the filter papers are weighed, and AMF rewet is determined.

Mean values are reported from measurements of ten representative samples.

Tested Samples

S-1: A topsheet of 23 gsm polypropylene spunbond nonwoven with a bulk of 10 cm³/g and an absorbent core layer formed from 140 gsm airlaid pulp fibres with a bulk of 9.8 cm³/g.

S-2: A topsheet of foam-formed hydroentangled cellulosic fibrous web material having a basis weight of 20 gsm and a bulk of 11.8 cm³/g and an absorbent core layer formed from 140 gsm airlaid pulp fibres and having a bulk of 9.7 cm³/g.

S-3: A topsheet of 23 gsm polypropylene spunbond nonwoven with a bulk of 9.9 cm³/g and an absorbent core layer formed from a foam-formed hydroentangled cellulosic fibrous web having a basis weight of 100 gsm and having a bulk of 6.4 cm³/g.

S-4: A topsheet of 23 gsm polypropylene spunbond nonwoven having a bulk of 10 cm³/g and an absorbent core layer formed from a foam-formed hydroentangled cellulosic fibrous web having a basis weight of 150 gsm and having a bulk of 5.9 cm³/g.

S-5: A topsheet of foam-formed hydroentangled cellulosic fibrous web material having a basis weight of 20 gsm with a bulk of 15 cm³/g and an absorbent core layer formed from a foam-formed hydroentangled cellulosic fibrous web having a basis weight of 100 gsm and having a bulk of 6.7 cm³/g.

S-6: A topsheet of foam-formed hydroentangled cellulosic fibrous web material having a basis weight of 20 gsm with a bulk of 16.6 cm³/g and an absorbent core layer formed from a foam formed hydroentangled cellulosic fibrous web having a basis weight of 150 gsm and having a bulk of 5.6 cm³/g.

S-7: A topsheet of 23 gsm dry creped tissue with a bulk of 8.1 cm³/g and an absorbent core layer formed from 140 gsm airlaid pulp fibres with a bulk of 10.0 cm³/g.

S-8: A topsheet of 35 gsm philic cotton spunlace nonwoven with a bulk of 18.4 cm³/g and an absorbent core layer formed from 140 gsm airlaid pulp fibres with a bulk of 10.1 cm³/g.

The cellulosic fibrous webs used in samples S-2 to S-6 were all produced in the same manner with the foam-forming process disclosed in WO 2018/065668 A1. All samples had the same fibre composition of 15% viscose, commercial 1.7 dtex 10 mm Danufil, Kelheim, and 85% unrefined bleached softwood kraft pulp. All samples were hydroentangled on the same equipment under comparable conditions.

The results of the tests are set out in Table 1.

|  | Rewet [g] | Spreading CD/width [mm] after 1$^{st}$, 2$^{nd}$ and 3$^{rd}$ liquid insult | | | Spreading MD/length [mm] after 1$^{st}$, 2$^{nd}$ and 3$^{rd}$ liquid insult | | |
|---|---|---|---|---|---|---|---|
| S-1 Ref. | 1.5 | 35 | 50 | 50 | 33 | 49 | 58 |
| S-2 | 1.7 | 30 | 45 | 50 | 32 | 46 | 59 |
| S-3 | 0.3 | 50 | 50 | 50 | 56 | 80 | 106 |
| S-4 | 0.02 | 45 | 50 | 50 | 48 | 70 | 96 |
| S-5 | 0.51 | 45 | 50 | 50 | 58 | 80 | 104 |
| S-6 | 0.24 | 40 | 50 | 50 | 50 | 68 | 90 |
| S-7 Ref. | 1.46 | 31 | 47 | 50 | 30 | 41 | 49 |
| S-8 Ref. | 1.62 | 24 | 36 | 48 | 34 | 45 | 58 |

**a liquid spreading value of 50 mm in the CD/width direction is an indication that liquid has spread in the width direction of the sample all the way to the longitudinal side edges of the sample.

As can be seen in Table 1, all the samples S-3 to S-6 which contain the foam-formed, hydroentangled cellulosic fibrous web materials disclosed herein as a core layer have excellent rewet and liquid spreading properties. It is noted that the samples S-1, S-2, S7 and S-8 having a conventional hydrophilic topsheet, a tissue topsheet or a conventional airlaid core layer had considerably higher rewet than the other samples.

The invention claimed is:

1. An absorbent hygienic article for absorbing body fluids, the article comprising a liquid permeable topsheet, a backing layer and an absorbent core arranged between the topsheet and the backing layer, the topsheet and the backing layer being made from roll materials, wherein the topsheet is constituted by a cellulosic fibrous web, the fibres in the cellulosic fibrous web being constituted by a mixture of cellulose fibres comprising regenerated cellulose fibres or natural cellulose staple fibres and cellulose pulp fibres, the cellulosic fibrous web being a foam-formed, hydroentangled fibrous web or in that an absorbent layer in the absorbent core is constituted by a cellulosic fibrous web, the fibres in the cellulosic fibrous web being constituted by a mixture of cellulose fibres comprising regenerated cellulose fibres or natural cellulose staple fibres and cellulose pulp fibres, the absorbent fibrous web being a foam-formed, hydroentangled fibrous web.

2. An absorbent hygienic article according to claim 1, wherein the regenerated cellulose fibres or the natural cellulose staple fibres are staple fibres having a length within the range of from 2 to 20 millimeter, and a fibre density in the range of from 0.3 to 3 dtex.

3. An absorbent hygienic article according to claim 1, wherein the mixture of cellulose fibres is a mixture of cellulose pulp fibres and viscose fibres.

4. A absorbent hygienic article according to claim 1, wherein the mixture of cellulose fibres is constituted by 2 to 50% by weight of regenerated cellulose fibres or natural cellulose staple fibres based on a total weight of the mixture of cellulose fibres.

5. An absorbent hygienic article according to claim 1, wherein the article has a rewet of less than 1 gram as measured according to the method disclosed herein.

6. An absorbent hygienic article according to claim 1, wherein the absorbent core comprises superabsorbent material.

7. An absorbent hygienic article according to claim 1, wherein the backing layer is constituted by renewable raw materials.

8. An absorbent hygienic article according to claim 1, wherein the absorbent hygienic article is a pantiliner, an incontinence protector, a sanitary napkin or an absorbent insert.

9. An absorbent hygienic article according to claim 1, wherein the absorbent hygienic article is a diaper.

10. An absorbent hygienic article according to claim 1, wherein a user-facing surface of the absorbent hygienic article web is provided with with a pattern, the pattern being an embossed pattern, a dimpling pattern, a printed pattern or a combination of one or more of an embossed pattern, a dimpling pattern, and a printed pattern.

11. An absorbent hygienic article for absorbing body fluids, the article comprising a liquid permeable topsheet, a backing layer and an absorbent core arranged between the topsheet and the backing layer, the topsheet and the backing layer being made from roll materials, wherein the topsheet is constituted by a cellulosic fibrous web, the fibres in the cellulosic fibrous web being constituted by a mixture of cellulose fibres comprising regenerated cellulose fibres and/or natural cellulose staple fibres and cellulose pulp fibres, the cellulosic fibrous web being a foam-formed, hydroentangled fibrous web.

12. An absorbent hygienic article according to claim 11, wherein the topsheet has a basis weight in the range of from 10 to 30 gsm.

13. An absorbent hygienic article according to claim 12, wherein the absorbent layer has a bulk in the range of from 8 to 10 cm$^3$/g.

14. An absorbent hygienic article according to claim 11, wherein an absorbent layer in the absorbent core is constituted by a cellulosic fibrous web, the fibres in the cellulosic fibrous web being constituted by a mixture of cellulose fibres comprising regenerated cellulose fibres or natural cellulose staple fibres and cellulose pulp fibres, the absorbent fibrous web being a foam-formed, hydroentangled fibrous web, the absorbent layer having a basis weight in the range of 30 to 150 gsm.

15. An absorbent hygienic article according to claim 14, wherein the absorbent layer is arranged in direct contact with the topsheet.

16. An absorbent hygienic article according to claim 11, wherein the topsheet has a bulk in the range of from 8 to 17 cm$^3$/g.

17. An absorbent hygienic article according to claim 11, wherein the absorbent hygienic article has a liquid spreading capacity in a machine direction of the cellulosic fibrous web of 75 millimeters or more as measured after three insults of test liquid in accordance with the test method disclosed herein.

18. An absorbent hygienic article according to claim 11, wherein the absorbent hygienic article has a liquid spreading capacity in a cross machine direction of the absorbent hygienic article of 30 millimeters or more as measured after a first insult of test liquid and of 45 millimeters or more as measured after two insults of test liquid, the measurements being made in accordance with the test method disclosed herein.

* * * * *